United States Patent [19]

Leise, Jr. et al.

[11] Patent Number: 5,167,651
[45] Date of Patent: Dec. 1, 1992

[54] TWO-PIECE OSTOMY APPLIANCE AND BISTABLE COUPLING RING THEREFOR

[75] Inventors: Walter F. Leise, Jr., Lindenhurst; Michael R. Lavender, Round Lake, both of Ill.

[73] Assignee: Hollister Incorporated, Libertyville, Ill.

[21] Appl. No.: 823,974

[22] Filed: Jan. 22, 1992

[51] Int. Cl.$^5$ .............................................. A61F 5/44
[52] U.S. Cl. ...................................... 604/339; 604/341
[58] Field of Search .................................. 604/337–342

[56] References Cited

U.S. PATENT DOCUMENTS

| | | | |
|---|---|---|---|
| 3,283,757 | 11/1966 | Nelson | 604/342 |
| 4,610,676 | 9/1986 | Schneider et al. | 604/339 |
| 4,610,679 | 9/1986 | Mohinddin | 604/341 |
| 5,088,992 | 2/1992 | Edwards et al. | 604/338 |

Primary Examiner—Randy C. Shay
Assistant Examiner—G. Gualtier
Attorney, Agent, or Firm—Tilton, Fallon, Lungmus

[57] ABSTRACT

A two-piece ostomy appliance in which one of the components, preferably the pouch component, is provided with a dual-state, bistable coupling ring for sealingly engaging the companion ring of the other (e.g., faceplate) component. The ring is formed of relatively stiff but flexible plastic material and is capable of assuming two stable states or conditions. In one such state, its normal one, the ring is substantially untensioned and its configuration is frusto-conical; in its other state, the direction of the conical taper is reversed or inverted and the ring again assumes a stable but now tensioned condition. When in its normal state, the ring has an inside diameter substantially smaller than in its inverted state, so that in mating such rings together, a user may enlarge the opening to facilitate joining the parts together and may then return the bistable ring to its normal state to insure a secure, fluid-tight seal between the parts.

15 Claims, 2 Drawing Sheets

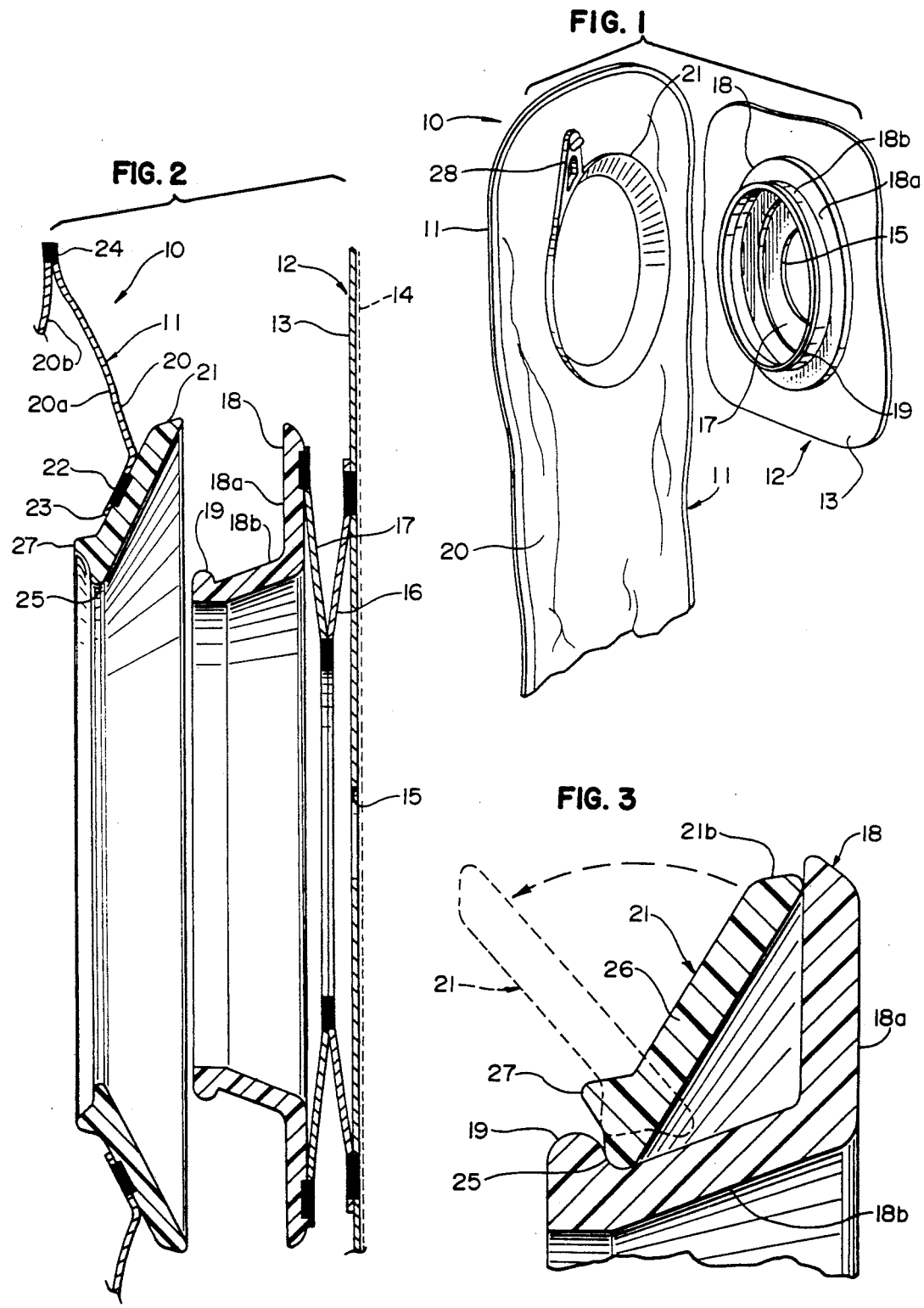

TWO-PIECE OSTOMY APPLIANCE AND BISTABLE COUPLING RING THEREFOR

BACKGROUND AND SUMMARY

Current two-piece ostmomy couplings generally require axial compressive force to secure a pouch ring to a faceplate ring. The application of axial force can cause wearer discomfort, since it ordinarily involves pressing the rings together against the body wall in the sensitive peristomal area, and may also be ineffective in producing proper latching and sealing engagement between the two coupling rings. Such rings can be unknowingly misaligned, resulting in accidental and/or premature disengagement. Also, the ability of conventional rings to produce an effective seal generally depends upon the extent of circumferential compression of the faceplate ring by the pouch ring. Typically, an element of the pouch ring stretches or deforms as it is applied over the faceplate ring, bringing such surfaces into leakproof contact. The problem has been to compromise the amount of circumferential compression (and therefore seal integrity) in order to ease the force required to fit a pouch ring into sealing engagement with a faceplate ring.

The present invention addresses this problem by providing one of the components, preferably the pouch component, with a coupling ring that is capable of being flexed into each of two stable conditions or states. In one such state, which may be considered the ring's normal untensioned state, the inside diameter of the ring is reduced to produce a fluid-tight circumferential seal about the mating part of the other coupling ring, whereas in its other state, the bistable ring has an enlarged inside diameter that facilitates joining of the coupling rings together. Thus, in use, the pouch coupling ring is flexed into its stable expanded (and tensioned) state so that little if any axial force is needed to fit the rings together and then, once the rings are in position, the bistable ring is simply flexed into its normal state of reduced inside diameter to produce fluid-tight interlocking engagement between the parts.

In its normal state, the bistable coupling ring is generally frusto-conical with the slope of its flange portion extending outwardly in one axial direction (preferably outwardly and away from the pouch upon which such a ring is mounted), whereas in its tensioned state of reduced inside diameter the ring is also frusto-conical but the direction of slope is reversed (i.e., axially outwardly towards the pouch). The inner periphery of the ring is circular in outline and rounded in axial section to provide a smooth annular lip for sealing engagement about that portion of the companion ring received in the opening. To maximize the difference between the inside diameters in the two stable states, the contractable/expandable coupling ring is provided with an integral rib located adjacent the sealing lip on the convex side of the ring when that ring is in its normal, untensioned condition. An integral tab portion may project radially outwardly beyond the circular outer periphery of the ring to facilitate manually directing the ring into each of its two stable states.

Other features, advantages, and objects will become apparent from the specification and drawings.

DRAWINGS

FIG. 1 is a perspective view of a two-piece ostomy appliance embodying this invention, the appliance being shown with the pouch component uncoupled from the faceplate component for clarity of illustration.

FIG. 2 is a somewhat schematic vertical sectional view illustrating the two-piece appliance with the components in uncoupled condition.

FIG. 3 is an enlarged fragmentary sectional view with the rings coupled together and illustrating in broken lines the action of the bistable ring as it is shifted into its unlatching position.

DETAILED DESCRIPTION OF PREFERRED EMBODIMENT

Figure 4:
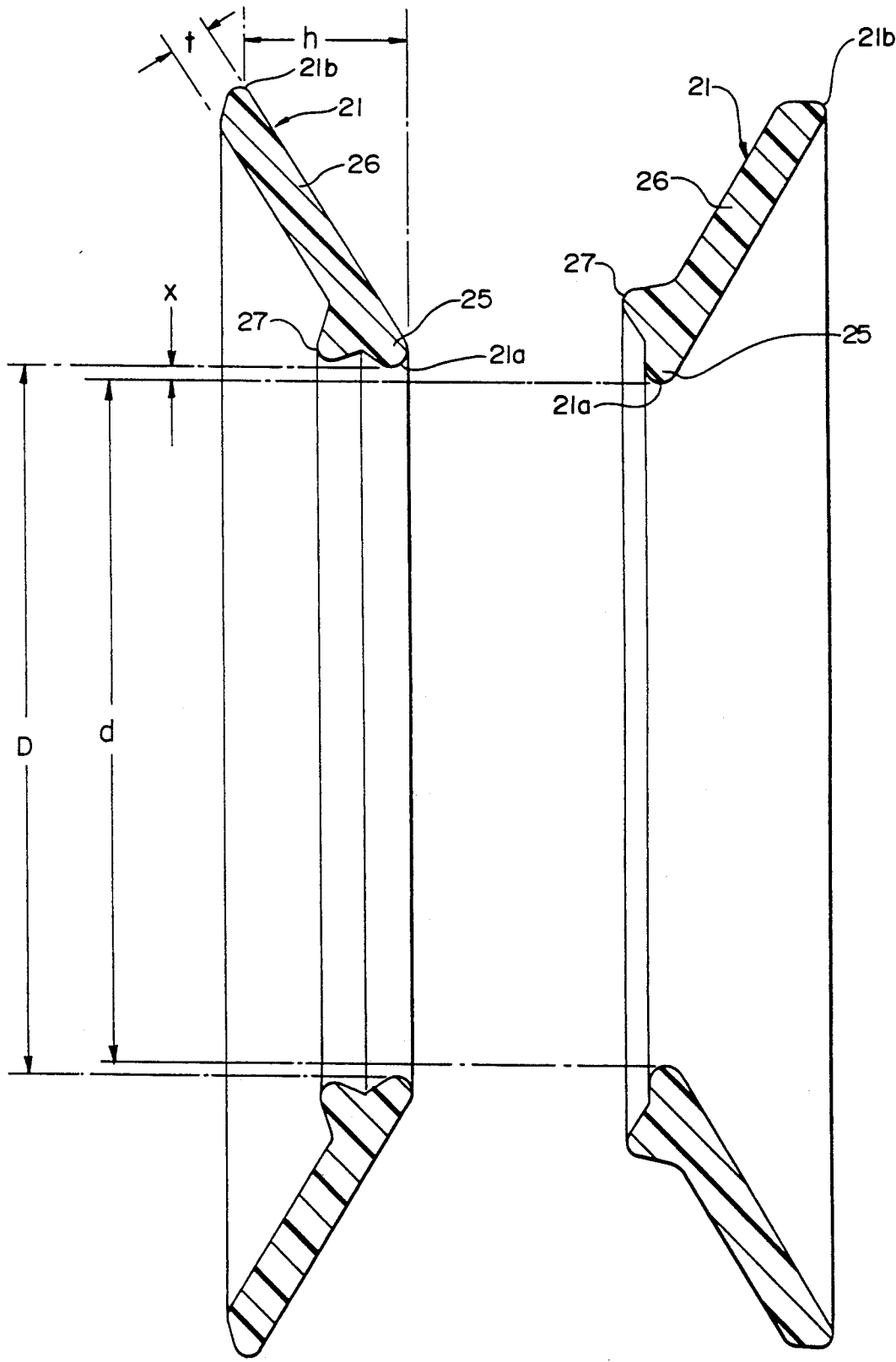
FIG. 4 depicts the bistable ring in each of its two stable states to illustrate the differences in inside diameter thereof.

In FIGS. 1 and 2, the numeral 10 generally designates a two-piece ostomy appliance comprising a pouch component 11 and a faceplate component 12. The faceplate component may be of known construction and comprises a flexible patch or panel 13 formed of microporous material or other suitable sheet material provided with a coating of pressure sensitive adhesive 14 along one surface for peristomal attachment to a patient. The faceplate has a stoma-receiving opening 15 which may be reformed or enlarged by cutting prior to application so as to conform generally with the size and shape of the patient's stoma. Annular webs 16 and 17 join the patch or panel 13 to faceplate coupling ring 18. While such a construction is preferred because it gives a limited "floating" action to the faceplate coupling ring 18 relative to adhesive patch 13, it will be understood that, if desired, coupling ring 18 may be joined directly to the patch by any appropriate means. Ring 18 may be formed of low density polyethylene or any other suitable polymeric material having similar properties of stiffness and limited flexibility and, as shown most clearly in FIGS. 2 and 3, has a generally planar radial portion 18a and an integral axial portion 18b terminating in an external bead or rib 19. For a more detailed description of faceplates and their coupling rings having similar features, reference may be had to co-owned U.S. Pat. Nos. 4,213,458, 4,419,100, 4,610,677, and 4,973,323.

The pouch component 11 comprises a pouch 20 and pouch coupling ring 21. Like ring 18, pouch coupling ring 21 may be formed of low density polyethylene or other polymeric material having similar properties of toughness, stiffness, and limited stretchability and flexibility. As shown in FIG. 2, ring 21 is heat sealed at 22 to one wall 20a of the pouch in an area surrounding pouch opening 23. The other wall 20b is peripherally sealed at 24 to wall 20a.

A characteristic feature of pouch ring 21 is that it is bistable—that is, the ring is predisposed to assume in spring-like fashion either of the two stable conditions or states depicted in FIGS. 3 and 4. In its normal, untensioned state, as shown to the right in FIG. 4, ring 21 is frusto-conical in shape, having concentric inner and outer peripheral edges 21a and 21b, respectively. The inner edge 21a is circular in outline and smoothly rounded in section to define an annular sealing lip 25 for engaging the outer surface of the axial portion 18b of faceplate ring 18 (FIG. 3). It will be noted that ring 21 has a relatively thin, outwardly and axially inclined annular flange portion 26 and that in its normal, untensioned state the slope of the flange portion is directed outwardly away from pouch 20 (FIG. 2). A rib 27 is formed as an integral part of the coupling ring and projects from that side of the ring facing pouch 20, in close proximity to lip 25.

The second stable condition of the coupling ring is illustrated on the left in FIG. 4. In its second state, the ring is again frusto-conical in shape but this time the slope is reversed with flange portion 26 extending outwardly and axially in the direction of pouch 20. Of particular importance is the fact that the inversion results in a significant increase in the inside diameter of the ring. In its normal, untensioned state, which may be its original molded state, ring 21 has a reduced inside diameter "d" as represented in FIG. 4, whereas in its other stable condition, in which it is under tension, the ring has an enlarged inside diameter "D." The difference in diameters is represented by "x" in FIG. 4. Because of such difference in inside diameters, the bistable ring may be regarded as asymmetrical in its bistability.

The difference in diameters results partly from the fact that in its normal state the ring is substantially untensioned whereas in its inverted state it is under hoop tension. The provision of integral rib 27 maximizes the dimensional difference between the diameters, with the rib acting as a circumferential fulcrum. The manner by which the inner diameter of the ring changes is believed to be as follows: As force is exerted on the ring to flex it from its normal untensioned state shown on the right in FIG. 4 into its inverted state, the lip 25 first begins to compress slightly and then, after the ring has passed an intermediate inversion plane, begins to stretch. During the same action, flange portion 26 at first stretches and then, beyond an inversion midplane, begins to contract. Since the mass of flange 26 is far greater than that of lip 25, the tension of the flange when the ring is in its inverted state results in a net stretching of the lip 25 and, hence, an enlargement of the opening defined by that lip.

The rib 27 contributes in maximizing the difference in diameters because it goes into compression as inversion begins. Being in close proximity to the thin stretched material of lip 25, the rib 27 acts as a point of leverage to promote stretching of the lip. Since a material such as low density polyethylene is inherently stronger in compression than in tension, the net result is a stretching and concurrent enlargement of the lip opening. Because rib 27 is located in close proximity to lip 25, the inversion results in the ring having an inside diameter at rib 27 which may be nearly as small as, but not smaller than, the diameter of the opening defined by lip 25.

The ratio between the thickness and axial length of coupling ring 21 have a bearing on the snap action or spring action of the ring into each of its stable states. From published information on Belleville (coned disk) springs, it is believed that the h/t ratio, axial height to thickness, of ring 21 (FIG. 4) should be substantially greater than 2.83.

When the bistable ring 21 is in its normal or untensioned state, the diameter of its opening as defined by lip 25 is slightly smaller than the outside diameter of the neck portion 18b of faceplate coupling ring 18. Conversely, when the rings are coupled together as shown in FIG. 3, lip 21 bears tightly against the outer surface of the neck portion 18b immediately adjacent shoulder 19. The interference fit results in fluid-tight sealing and latching engagement between the parts. The outer perimeter 21b of ring 21 may contact radial portion 18a and, to facilitate such bracing contact, ring 21 may have an outer perimeter slightly smaller than that of ring 18 except for a flexible tab portion 28 that projects radially outwardly from ring 21 (see FIGS. 3 and 1). When uncoupling of the rings is desired, the user grasps the radially-projecting tab 28 and urges it axially towards the pouch, thereby reversing or inverting ring 21 as indicated in broken lines in FIG. 3. The inversion results in enlargement of the opening of ring 21 with the opening assuming a diameter more closely approaching that of shoulder 19 and permitting the ring 21 to be pulled clear of the shoulder. Thus, assembly and disassembly of the rings may be easily accomplished with ring 21 in its stable but tensioned state but, because the bistability of the ring, a secure, fluid-tight connection is achieved simply by pivoting ring 21 into its normal and substantially untensioned state when the parts have been fitted together as depicted in FIG. 3.

While in the foregoing, we have disclosed an embodiment of the invention in considerable detail for purposes of illustration, it will be understood by those skilled in the art that many of these details may be varied without departing from the spirit and scope of the invention.

We claim:

1. A bistable spring-action coupling ring for an ostomy appliance, said ring being formed of relatively stiff but flexible plastic material and having concentric inner and outer edges of generally circular configuration; said ring having a stable and substantially untensioned normal frusto-conical state in which said inner edge defines an opening of a predetermined first diameter and being flexible into a stable but tensioned inverted frusto-conical state in which said opening has a diameter larger than said first diameter.

2. The ring of claim 1 in which said ring includes a flange portion that slopes in one axial direction when said ring is in its normal frusto-conical state and in an opposite axial direction when said ring is in its inverted frusto-conical state.

3. The ring of claim 2 in which said flange portion is circumferentially sealed to a flexible wall of an ostomy pouch about a stoma-receiving opening in said wall.

4. The ring of claim 2 in which tab means projects radially outwardly from said outer edge of said ring for manually directing said ring between its untensioned normal state and its tensioned inverted state.

5. The ring of claims 2, 3, or 4 in which said ring includes a rounded lip portion defining said opening; said ring also having an integral rib portion projecting from said flange portion along a side thereof facing in said opposite axial direction and adjacent to said lip portion.

6. The ring of claim 2 in which said flange portion has an axial height to thickness ratio of more than 2.83.

7. An ostomy pouch having a thin, flexible wall provided with a stoma-receiving opening therein; and a bistable spring-action coupling ring circumferentially secured to said wall about said opening; said ring being formed of relatively stiff but flexible plastic material and having concentric inner and outer edges of generally circular configuration; said ring also having a stable and substantially untensioned normal frusto-conical state in which said inner edge defines an opening of a predetermined first diameter and being flexible into a stable but tensioned inverted frusto-conical state in which said opening has a diameter larger than said first diameter.

8. The pouch of claim 1 in which said ring includes a thin flange portion that slopes outwardly away from said pouch when said ring is in its normal frusto-conical state and towards said pouch when said ring is in its inverted frusto-conical state.

9. The pouch of claim 8 in which said flange portion includes a rounded lip portion defining said opening; said ring also having an integral rib portion projecting from said flange portion adjacent to said lip portion and from a side of said flange portion facing said pouch.

10. The pouch of claim 7 in which tab means projects radially outwardly from said outer edge of said ring for manually directing said ring between its untensioned normal state and its tensioned inverted state.

11. A two-piece ostomy appliance comprising a pouch component and a faceplate component equipped respectively with pouch and faceplate coupling rings for detachably connecting said components together; said faceplate coupling ring including a neck portion having a smooth, annular, outwardly-facing surface; said pouch coupling ring being formed of relatively stiff but flexible plastic material and having concentric inner and outer edges of generally circular configuration; said pouch coupling ring being bistable and having a stable and substantially untensioned normal frusto-conical state in which said inner edge defines an opening of a predetermined first diameter smaller than the diameter of the annular outwardly-facing surface of said neck portion and a stable but tensioned inverted frusto-conical state in which said opening has a diameter larger than said first diameter.

12. The appliance of claim 11 in which said pouch coupling ring includes a flange portion that slopes outwardly away from said pouch when said pouch ring is in its norma frusto-conical state and towards said pouch when said pouch ring is in its inverted frusto-conical state.

13. The appliance of claim 12 in which said pouch ring includes a lip portion defining said opening and sealingly engagable with said outer annular surface of said neck portion when said rings are fitted together and said bistable pouch ring is in its normal state.

14. The appliance of claim 13 in which said pouch ring also includes an integral rib portion adjacent to said lip portion and projecting from a side of said flange portion facing said pouch.

15. The appliance of claim 11 in which tab means project radially outwardly from said outer edge of said pouch ring for manually directing said bistable pouch ring between its untensioned normal state and its tensioned inverted state.

* * * * *